United States Patent
Zarate et al.

(10) Patent No.: US 6,806,455 B2
(45) Date of Patent: Oct. 19, 2004

(54) IMAGING FLUOROMETER FOR TIME RESOLVED FLUORESCENCE

(75) Inventors: Carlos Zarate, Hamilton (CA); Paul Donders, Stoney Creek (CA); Ahmad Yekta, St. Catharines (CA); Zahra Masoumi, St. Catharines (CA); Peter Ramm, St. Catharines (CA)

(73) Assignee: Imaging Research Inc., St. Catharines (CA)

( * ) Notice: Subject to any disclaimer, the term of this patent is extended or adjusted under 35 U.S.C. 154(b) by 199 days.

(21) Appl. No.: 10/240,615
(22) PCT Filed: Feb. 27, 2002
(86) PCT No.: PCT/IB02/00590
§ 371 (c)(1),
(2), (4) Date: Sep. 30, 2002
(87) PCT Pub. No.: WO02/068942
PCT Pub. Date: Sep. 6, 2002

(65) Prior Publication Data
US 2003/0160151 A1 Aug. 28, 2003

Related U.S. Application Data
(60) Provisional application No. 60/272,083, filed on Feb. 28, 2001.

(51) Int. Cl.$^7$ ............................................. H01L 27/00
(52) U.S. Cl. .................................... 250/208.1; 250/573
(58) Field of Search ............................ 250/208.1, 216, 250/573, 574, 576, 458.1, 461.2; 356/417; 422/52, 65; 436/172, 48

(56) References Cited

U.S. PATENT DOCUMENTS 6,740,890 B1 * 5/2004 Tai ........................... 250/458.1

FOREIGN PATENT DOCUMENTS

| EP | 0 987 540 | 3/2000 |
|---|---|---|
| WO | WO 99/08233 | 2/1999 |
| WO | WO 00/06990 | 2/2000 |

OTHER PUBLICATIONS

Verwoerd, N. P. et al., "Use of Ferro–Electric Liquid Crystal Shutters for Time–Resolved Fluorescence Microscopy." Cytometry: The Journal of the Society for Analytical Cytology. United States. Jun. 1, 1994, vol. 16, No. 2, pp. 113–117, XP002216380.

Edmiston, Paul L. et al., "Temporary Gating a Slow–Scan CCD with a Liquid Crystal Shutter." Applied Spectroscopy, The Society for Applied Spectroscopy. Baltimore, United States, vol. 47, No. 2, Feb. 1, 1993, pp. 250–253., XP000338527.

International Search Report.

* cited by examiner

Primary Examiner—Que T. Le
(74) Attorney, Agent, or Firm—Darby & Darby

(57) ABSTRACT

The present invention relates to an apparatus and method for imaging time resolved fluorescence in biochemical and medical samples. In a primary aspect, the device includes a lens of large aperture, a flash lamp in the illumination path, a fast-acting solid state shutter or a gated detector in the emission path, a device for delivering homogenous monochromatic illumination to a plurality of wells distributed within a microwell plate, a digital camera of high quantum efficiency, and a computer under computer control, the lamp is pulsed at short intervals. The fast-acting emission shutter or gated detector operates to limit exposure of the camera to a period some microseconds after the extinction of each lamp pulse, during which only delayed fluorescence is transmitted to the camera. The invention achieves simultaneous time resolved imaging of a plurality of samples, with high sensitivity and high throughput.

30 Claims, 6 Drawing Sheets

IMAGING FLUOROMETER FOR TIME RESOLVED FLUORESCENCE

CROSS REFERENCE TO RELATED APPLICATIONS

This application claims priority under 35 U.S.C. §119(e) based upon U.S. Provisional Application Ser. No. 60/272,083 filed Feb. 28, 2001, the entire disclosure of which is hereby incorporated by reference.

FIELD OF THE INVENTION

The present invention relates to an apparatus and method for imaging time resolved fluorescence in biochemical and medical samples.

BACKGROUND OF THE INVENTION

Fluorescence is emitted when a fluorophore interacts with an incident photon (excitation). Absorption of the photon causes an electron in the fluorophore to rise from its ground state to a higher energy level. After a time dependent on the fluorophore and its environment, the electron reverts to its original level, releasing a photon (fluorescence emission) with wavelength dependant upon the amount of energy that is released during reversion. A fluorophore may emit at single or multiple wavelengths (creating an emission spectrum), as electrons drop from various orbitals to their ground states. The emission spectrum is constant for each species of fluorophore.

Fluorescent labels typically are small organic dye molecules, such as fluorescein, Texas Red, or rhodamine, which can be readily conjugated to probe molecules, such as steptavidin. The fluorophores can be detected by illumination with light of an appropriate excitation frequency and the resultant spectral emissions can be detected by electro-optical sensors or by eye.

Methods of performing assays on fluorescent materials are well known in the art and are described in, e.g., Lakowicz, J. R., Principles of Fluorescence Spectroscopy, New York: Plenum Press (1983); Herman, B., Resonance Energy Transfer Microscopy, in: Fluorescence Microscopy of Living Cells in Culture, Part B, Methods in Cell Biology, vol. 30, ed. Taylor, D. L. & Wang, Y.-L., San Diego: Academic Press (1989), pp. 219–243; Turro, N. J., Modem Molecular Photochemistry, Menlo Park: Benjamin/Cummings Publishing Co, Inc. (1978), pp. 296–361 and the Molecular Probes Catalog (2001), OR, USA.

A fluorometer is an instrument that measures fluorescence. Fluorometers have three principal components: (a) light source for excitation, which is most typically a laser or broadband source; (b) filters and/or dispersive monochromators for selecting wavelength regions of interest, both in excitation and in emission; (c) a detector which converts the impinging fluorescence emission to an electrical signal. The present invention relates to fluorometers which measure fluorescence in biological samples, most specifically in biological samples used in drug discovery programs.

Some fluorometers (micro fluorometers) are constructed around confocal or noconfocal microscopes, and are designed for viewing fluorescently labeled cells or microvolumes of sample as discrete targets. There is a massive body of prior art relevant to such micro fluorometers. A subset body of this body of prior art relates to the use of micro fluorometers with microwell plates or wafers (e.g. Galbraith, et al., 1991; Rigler, 1995).

Other fluorometers (macro fluorometers) do not measure at cellular resolution but, rather, use low magnification optics to collect signal from each sample in a plurality of samples (as in U.S. Pat. No. 5,125,748 to Bjornson et al.; U.S. Pat. No. 5,340,747 to Eden), most typically wells are arranged within microwell plates (as in U.S. Pat. No. 6,071,748 to Modlin et al.; U.S. Pat. No. 5,670,113 to Akong et al.).

The means by which a plurality of samples is measured differs between a "scanning fluorometer", a "stepping fluorometer" and an "area imaging fluorometer".

In a scanning macro fluorometer (as disclosed in U.S. Pat. No. 5,672,880 to Kain), a plurality of samples is detected in serial fashion, by scanning an excitation beam over the sample and collecting each emission point serially. A scanning fluorometer can resolve each sample into multiple resolution points.

In a stepping macro fluorometer, the excitation beam and the detector (usually a photomultiplier tube or diode) move in stepwise fashion from sample to sample. The detector (or array of detectors) makes a unitary measurement from each sample, and does not discriminate multiple resolution points within each sample (as e.g. U.S. Pat. No. 5,589,351 to Harootunian; U.S. Pat. No. 5,670,113 to Akong et al.; U.S. Pat. No. 6,144,455 to Tuunanen et al; U.S. Pat. No. 6,127,133 to Akong et al.).

In an area imaging macro fluorometer, the detector is exposed to a plurality of samples in parallel (without scanning or stepping), and each sample is detected on a different portion of the detector area. By localizing different samples to different points on the detector, the area imaging fluorometer maintains the ability to discriminate discrete samples within a plurality of samples. The area imaging macro fluorometer may or may not discriminate multiple resolution points within each sample.

Area imaging macro fluorometers are well known (e.g. Haggart 1994; U.S. Pat. No. 6,140,653 to Che; U.S. Pat. No. 6,069,734 to Kawano et al.; many commercial systems). Most of these are suitable for flat samples such as electrophoresis gels. Some (e.g. U.S. Pat. No. 5,275,168 to Reintjes et al.; U.S. Pat. No. 5,309,912 to Knuttel) require highly specialized methods such as Raman spectroscopy or phase/amplitude modulation of illumination, and would not be suitable for either prompt or time resolved fluorescence intensity measurements as used with a plurality of biological samples. Others (U.S. Pat. No. 5,854,684 to Stabile et al.) mention the general use of imaging detectors to quantify light reflected from a plurality of samples, without describing specific embodiments within the illumination and optical detection systems that would allow effective use of the imaging detectors in macro fluorometry. Finally, others (WO96/05488 to McNeil et al.) disclose specific means to accomplish area imaging macro fluorometery, which means are not optimal for the purpose.

There is a need for high rates of sample throughput in drug discovery applications, wherein fluorescent specimens are usually arrayed within a plurality of wells and high throughput is required. While an area imaging fluorometer offers known advantages in its ability to quantify large numbers of samples in parallel, thereby achieving high throughput, specific embodiments appropriate to this purpose are required if the instrument is to be both high in throughput and high in sensitivity.

It is obvious, in light of the art of area imaging macro fluorometers, to position a CCD camera so as to image a specimen, deliver fluorescence excitation by known means, and collect emitted light using a lens in a known fashion. However, imaging fluorometers of the kind disclosed by McNeil et al. (WO96/05488) do not achieve equivalence in sensitivity with non-imaging fluorometers, and suffer from errors in signal detection. For example, they use standard lens systems which do not contain mechanisms so calculated as to minimize reflections and other forms of spurious signal, suffer from parallax error, and usually require that microwell plates be of the kind with a transparent bottom, through which the samples are read. In contrast, non-imaging fluorometers are highly sensitive, have no parallax error, are able to read from top or bottom of a plate, and do not require expensive transparent-bottom plates. Potential users of area imaging fluorometers in drug screening have not adopted widely any prior art system, because of factors such as those detailed above.

Challenges in applying area imaging fluorometry to drug screening arise, in the main, from four factors:

a) The wells form apertures which interact with the angle of incidence of the illumination. Wells which receive illumination at greater angles are less well illuminated than wells which receive more direct illumination. As most area imaging fluorometers deliver illumination from a region lateral to the collection lens (e.g. Neri et al., 1996), they can be successful with flat specimens but fail to properly illuminate deep wells. In practice, it is not uncommon to observe variations in excess of 300% in the delivery of light to wells lying at different positions in a microwell plate unless illumination delivery occurs only through the bottom of the microwell plate (as in U.S. Pat. No. 5,355,215 to Schroeder and WO96/05488 to McNeil et al.).

b) The wells are very dim. A plurality of wells contained within a standard microwell plate occupies a spatial extent of approximately 96 cm sq. If a macro area imaging fluorometer is to be capable of imaging all wells in parallel, all the wells must be illuminated at the same time. Therefore, the amount of illumination delivered to any one well (as described by an inverse geometric relationship between illuminated area and intensity/unit area) is very low and the amount of fluorescence emitted from any one well also tends to be small and a sensitive detector is required. However sensitive the detector, it is important that all wells receive the illuminating beam as efficiently as possible. If illumination fails to reach the contents of some wells, even the most sensitive detector will be unable to extract a usable signal.

c) There is parallax error. Deep wells located at different positions within a microwell plate are imaged at different angles by a standard lens. This well known parallax error has a major effect upon the accuracy of the light collection optic, particularly when the optic images the plurality of wells from the top.

d) The illumination rays interact with the detection optics. Optics for illumination delivery to an entire well plate, and for simultaneous collection of fluorescence emission from the plurality of wells in the plate must have special properties. For example, the most efficient illumination method is from within the collecting lens (epi-illumination), but a macro epi-illuminating lens is subject to reflections and other non-obvious sources of spurious signal.

A digital system imaging system for assays in well plates, gels and blots is disclosed in U.S. patent application Ser Nos. 09/240,649 and 09/477,444 by Ramm et al. This system meets the need for high throughput area imaging fluorometry, and achieves a technical advance in that it overcomes the problems raised in points a–d, above. Most specifically, the disclosed system:

a) minimally interacts with the well apertures so as to illuminate a plurality of wells in an efficient and even fashion, whether from above or below;

b) by illuminating in an efficient manner, allows better sensitivity in area imaging fluorometry;

c) uses a telecentric optic to avoid parallax error;

d) contains optics and components calculated to minimize sources of background signal arising in macro area imaging fluorometry (e.g. minimizes internal reflections from emission filters mounted within the collection lens).

The disclosed system has been reduced to practice and widely used for area imaging of luminescence and prompt fluorescence signals. Means to use the system for time resolved fluorescence imaging are disclosed in the cited patent applications, but without detailed description of the embodiments for this purpose. The present invention discloses preferred embodiments of an area imaging fluorometer for time resolved assays in well plates, gels and blots.

Prompt fluorescence emission is defined by the delivery of excitation illumination at the same time as emitted fluorescence is collected. Challenges in prompt fluorescence include:

very small alterations in emission must be detected while the system is flooded with excitation light;

emission is much lower in intensity than excitation, and it is difficult to filter out all of the excitation so as to leave uncorrupted emission;

the sample medium (e.g. solvent, cells containing labeled compound), optics (e.g. Beverloo et al. 1990, 1992) and sample carrier (well plate, cuvette) can emit spectral components similar to those of the fluorophore of interest.

Collectively, any excitation light or sample medium contributions that reach the detector are termed "background". An emission filter is placed between the sample and the detector so as to block as much as possible of the background signal from reaching the detector (as disclosed in International Patent Application Publication WO99/08233 to Ramm et al.). However, the emission filter cannot remove all of the background and the remaining leakage of background onto the detector results in a degradation in detection sensitivity. That is, the sensitivity of fluorometers tends to be limited by the presence of high levels of background signal.

Time resolved fluorescence (TRF) is a well-known technique (e.g. U.S. Pat. No. 4,565,790 to Hemilla et al., U.S. Pat. No. 4,808,541 to Mikola et al., U.S. Pat. No. 5,736,410 to Zarling et al.) used to reduce background and increase detection sensitivity. In TRF, a light source is used to excite the sample and is then quickly extinguished or occluded. During the period of excitation, the detector is turned off. Being off, it is not subject to background contributions arising from the period of excitation (e.g. leakage of the excitation light through the emission filter).

Most background contributions are absent or decay rapidly (e.g. solvent fluorescence) after termination of excitation. In contrast, fluorophores do not cease their emission immediately. Rather, there is a period (ranging from picoseconds to milliseconds) during which the fluorophore continues to emit after the excitation is terminated. During this period, the detector is turned on to observe relevant fluorescence signal with minimal background. This delayed timing of the detection period is the key principle of TRF.

To enable TRF detection, the detector must be turned on and off within a controlled time period. The detection period starts some time after termination of excitation (after a delay time) and lasts for a period of time (the acquisition time). TRF is most often used with fluorophores based on lanthanides (Eu, Tb, etc.), that have decay times of the order of 100 microseconds to 2 milliseconds, much longer than the typical decay times of the background sources. Typically, the delay time is on the order of tens of microseconds, and the acquisition time is tens to hundreds of microseconds.

During the excitation period and the delay time, the detector is occluded or turned off (hereinafter referred to as gated off). During the acquisition time, the detector is exposed to emissions from the sample (hereinafter referred to as gated on). It is unlikely that any single cycle of gating off and gating on will generate a reliable signal on the detector, so the cycle is repeated until sufficient signal has accumulated.

Delayed fluorescence emission is much less intense than prompt fluorescence emission, and area imaging systems must work with very low levels of emission/unit area. Therefore, an area imaging fluorometer is more subject to the loss of delayed emission in the noise floor of the detector than is another type of fluorometer. Hence, it is desirable for a TRF system to have a geometry which results in high optical throughput (etendue) and low transmission losses. Challenges arise in optimizing a system to achieve this combination of rapid gating and high etendue.

Both the excitation light and the detector must be gated. Gating of excitation with mechanical choppers and/or by using pulse lasers (e.g. Gadella and Jovin, 1995) is widely known, as is use of flash lamps which decay quickly enough that their contribution to the delayed acquisition is minimal (as disclosed in WO 99/08233 to Ramm et al.; EP 0987540A2 to Vaisala et al.; Vereb et al. 1998).

There are three methods in common use for the gating of the emission pathway in TRF:

(a) A shutter wheel is rotated rapidly to produce microsecond-scale gating of the emitted light. This approach has been applied in TRF microscopy (Seveus et al., 1992) to reject the signal from prompt fluorescence and thereby reduce autofluorescence. A similar method is disclosed in EP 0626575A1 to Vaisala et al., and in scanning detection systems (U.S. Pat. No. 5,780,857 to Harju, et al). On a microscope or a system which detects one sample at a time, a single fast shutter is viable because the etendue is very small. In contrast, the etendue of macro imaging systems is large, about two orders of magnitude greater than that of a microscope. A macro imaging system would require a large mechanical shutter mechanism, which has a relatively gradual transition from open to closed.

(b) A multicomponent mechanical shutter, using fast rotating shutter wheels has openings synchronized in such a way to expose small sections of the detector at a time. This arrangement, (as disclosed in EP 0987540A2 to Vaisala et al.) is faster than a single wheel, but is complex, composed of rapidly moving parts, and has poor etendue.

(c) The detector is gated, electrically, and also converts emission photons into electrons. In this method a photocathode is placed into the optical path. The photocathode can be turned on and off at short intervals to accommodate the timing requirements of TRF. However, this type of device has low quantum efficiency and could not be used to image dim fluorescence emission onto an imaging detector. Therefore, an accelerating electrical field is applied to increase the energy of the photoelectrons prior to the target and, in many cases the accelerated electrons are guided through a microchannel plate, where they initiate the emission of many more accelerated electrons. Thus, the electrically gated detector usually incorporates a light amplifier, which amplifies the electron stream prior to the target.

A macro TRF imaging system using an electrically gated detector, with a photocathode and microchannel plate amplification has been disclosed (WO 99/08233, Ramm et al; Ramm, 1999). The use of an amplified photocathode between the lens and the detector has inherent disadvantages:

(a) Most typically, TRF is emitted at long wavelengths. This is particularly true with donor-acceptor pairs in fluorescence resonance energy transfer (FRET), which tend to emit in the red portion of the spectrum. To detect these types of signals, the bandgap of the photocathode needs to be sufficiently low to allow a long wavelength photon to generate a photoelectron. However, low bandgap materials are prone to generate thermal signals and produce an instrumental background that can be indistinguishable from the signal to be detected. Mildly cooling the photocathode (as reduced to practice in commercially available devices) does not eliminate thermal background. Deep cooling of the photocathode to temperatures sufficiently low to greatly reduce thermal background presents significant technological challenges and is not in common use.

(b) The camera component of an intensified system produces noise, particularly thermal background. To overcome this, the CCD can be cooled to reduce thermal background (as reduced to practice in a number of commercial devices). Difficulties reside in cooling a fiber-coupled CCD that is absorbing heat load from an intensifier, and in maintaining a bond between the warm fiber coupling and the cold CCD.

(c) The QE of the gating/amplification component is low, typically on the order of 10% in blue-green wavelengths, and as low as 1% in the red. Therefore, most of the signal incident to the amplified gating system is lost, and use of the system with time resolved fluors emitting in the red is problematic.

(d) The amplification process does not produce a constant number of electrons per incident photoelectron. This gain noise is, typically, overcome by setting a minimum threshold for detected events, and counting only events which have a high probability of being valid. In this way, the amplified device is operated as a counter, instead of as an integrating imager. While highly sensitive in this counting mode, the amplified device is also very inefficient and long periods of detection are required to accumulate enough suprathreshold events to create an image.

There are other disadvantages, including fragility of the light amplifier (it is easily destroyed by bright lights) and poor modulation transfer in the amplified images. Further, bright areas of the specimen will tend to influence areas around them and, therefore, imaging of microwell plates is highly subject to crosstalk between wells. In sum, prior art systems using photocathode gating and amplification all exhibit shortcomings in the field of the present invention.

It is possible to construct a macro area imaging fluorometer for TRF, in which the gating and amplification functions are inherent to the detector. For example, it has been determined that an electron bombarded CCD (EBCCD) can be implemented within a system of the configuration disclosed by Ramm et al. (WO 99/08233). It is envisaged that other integrally amplified detectors, such as the electron amplifying CCD (as reduced to practice by Marconi Applied Technologies of the United Kingdom), would also be applicable within a system of the disclosed configuration. In comparison to intensified CCD cameras, it is an advantage of the EBCCD (and perhaps other integrally gated detectors) that it shows very little crosstalk in imaging microwell plates, while it remains sensitive enough to detect faint delayed fluorescence signals.

Almost any type of fast shutter could be envisaged as a gate for a TRF system. TRF with a macro epi-illuminating system using a liquid crystal, leaf or other shutter mounted within the optical path after the specimen but prior to the detector has been disclosed (WO 99/08233, Ramm et al.). In a preferred embodiment, the present invention incorporates such a shutter implemented within a system which is so optimized as to allow its use.

While automation of the process by which the present invention is applied is not specifically described, it can be envisaged that the present invention can be used with systems and methods that utilize automated and integratable workstations for identifying modulators, pathways, chemicals having useful activity and other methods described herein. Such systems are described generally in the art (see, U.S. Pat. No. 4,000,976 to Kramer et al. (issued Jan. 4, 1977), U.S. Pat. No. 5,104,621 to Pfost et al. (issued Apr. 14, 1992), U.S. Pat. No. 5,125,748 to Bjornson et al. (issued Jun. 30, 1992), U.S. Pat. No. 5,139,744 to Kowalski (issued Aug. 18, 1992), U.S. Pat. No. 5,206,568 Bjornson et al. (issued Apr. 27, 1993), U.S. Pat. No. 5,350,564 to Mazza et al. (Sep. 27, 1994), U.S. Pat. No. 5,589,351 to Harootunian (issued Dec. 31, 1996), and PCT Application Nos: WO 93/20612 to Baxter Deutschland GMBH (published Oct. 14, 1993), WO 96/05488 to McNeil et al. (published Feb. 22, 1996) and WO 93/13423 to Agong et al. (published Jul. 8, 1993).

In accordance with the present invention, an area imaging system for time resolved fluorometry of samples in well plates, gels, and blots incorporates a fast-acting electronic emission shutter implemented within a strobe-illuminated system of large etendue, coupled to a camera of high sensitivity (preferably as disclosed in WO 99/08233 to Ramm et al.). Preferably, but not necessarily, the emission shutter of the system is based upon ferroelectric crystal (FLC) technology. The FLC shutter is a ferroelectric-based device composed of an input polarizer, a ferroelectric material that changes the rotation of polarization depending on the electric field, and a polarizing analyzer inserted in the emission path of array imaging systems, between the sample and a solid state array detector.

It is a property of the system of the present invention that the optical/detection components containing the FLC shutter are so sensitive that transmission loss through the electronic shutter is accommodated without requiring a light amplification stage. In a preferred configuration, the quantum efficiency of the detector is high and the etendue of the optics is large. When used within such a system, the shutter of the present invention transmits enough delayed fluorescence to yield measurements comparable to those obtained from non-imaging time resolved fluorometers, and exceeds the sensitivity of systems using amplified photocathodes without the disadvantages (crosstalk, fragility, etc.) of such systems.

One skilled in the art will appreciate that a fast electronic shutter would be useful as a gating mechanism for TRF. However, most fast shutters like Kerr cells, opto-acoustical modulators or electro-optical modulators, have limited etendue restricting their applications to systems with small etendue like microscopes. It is an advantage of the electronic shutter of the present invention that it has a large aperture and takes advantage of the etendue of the system of the present invention.

The system of the present invention could be equipped with a liquid crystal-based shutter. While this type of shutter can have a sufficient aperture to be used with the large etendue of the present system, it has a poor ratio of the transmissive state to the blocking state (defined as contrast ratio). Most typically, the contrast ratio of a liquid crystal shutter is on the order of <200:1, as compared to the >400:1 observed with an FLC shutter. The liquid crystal-based shutter is also not sufficiently fast for TRF imaging with many commonly used fluors.

Preferably, the system of the present invention incorporates a ferroelectric crystal-based (FLC) shutter. It is an advantage of the system of the present invention that the FLC shutter can transit from gated on to gated off within less than 100 microseconds, and is suitable for delayed fluorescence imaging of commonly used lanthanide, europium and terbium fluors.

The disadvantage of FLCs, as disclosed in previous attempts to use FLC shutters in TRF microscopy, has been poor rejection of the prompt fluorescence due to an inadequate contrast ratio (Verwoerd et al., 1994; Shotten, 1995). This poor contrast ratio has forced the use of two FLC shutters in series, and the resulting transmission loss has been so high (Vereb et al., 1998) that use in a macro imaging fluorometer would be impossible. In the present invention, the FLC is placed within the optics, in a position to yield the best possible contrast ratio. It is a property of the system of the present invention that the optics are so constructed that the fast shutter is positioned in the optical path of the emitted fluorescence in such a manner that the incidence angles with respect to the normal onto the shutter do not exceed 20°. This positioning achieves the best possible contrast ratio from the shutter, and minimizes the effects of said shutter upon the wavelength characteristics of the transmitted light.

In a preferred embodiment of the present invention, leakage through the FLC shutter is corrected by first taking an image of prompt fluorescence with the shutter closed (the leakage image). This image is read out from the CCD camera, prior to acquisition of the delayed fluorescence image. Then, the leakage image is subtracted from the delayed fluorescence image to leave an image of delayed fluorescence without background added by leakage through the FLC shutter.

It is an advantage of the illumination system and electronic shutter of the present invention that they can be adapted to use in existing macro area imaging fluorometers, without requiring major modifications to said devices (e.g. as disclosed in WO 99/08233, Ramm et al.). Rather, the illumination system of the present invention can be mounted within an existing macro area imaging fluorometer, and the shutter can also be mounted within said device without major modification.

It is an advantage of the present invention that the shutter is easily inserted or removed from a macro area imaging fluorometer, allowing said fluorometer to be used for a very broad variety of applications without interference from said shutter.

It is an advantage of the system of the present invention that it can be used with systems and methods that utilize automated and integratable workstations for identifying modulators, pathways, chemicals having useful activity and other methods described herein. Such systems are described generally in the art (see, U.S. Pat. No. 4,000,976 to Kramer et al. (issued Jan. 4, 1977), U.S. Pat. No. 5,104,621 to Pfost et al. (issued Apr. 14, 1992), U.S. Pat. No. 5,125,748 to Bjornson et al. (issued Jun. 30, 1992), U.S. Pat. No. 5,139,744 to Kowalski (issued Aug. 18, 1992), U.S. Pat. No. 5,206,568 Bjornson et al. (issued Apr. 27, 1993), U.S. Pat. No. 5,350,564 to Mazza et al. (Sep. 27, 1994), U.S. Pat. No. 5,589,351 to Harootunian (issued Dec. 31, 1996), and PCT Application Nos: WO 93/20612 to Baxter Deutschland GMBH (published Oct. 14, 1993), WO 96/05488 to McNeil et al. (published Feb. 22, 1996) and WO 93/13423 to Akong et al. (published Jul. 8, 1993).

While the present invention is directed at time resolved macro fluorescence area imaging, it is to be understood that one skilled in the art could use the polarization capabilities of the present invention, as embodied in the FLC shutter or other shutter incorporating polarizing optics, to construct a polarization macro fluorescence area imaging system. In such system, the excitation light is polarized by first passing through a FLC shutter or some other polarizing device. The emitted light is passed through a polarizer mounted within the emission path. Either polarizer may be rotated with respect to the other, and the system is of such high sensitivity that it achieves polarization measurement comparable to that of non-area imaging devices.

BRIEF DESCRIPTION OF THE DRAWINGS

The foregoing and other objects, features and advantages of the present invention will be understood more completely from the following description of presently preferred, but nonetheless illustrative embodiments in accordance with the present invention, with reference being had to the accompanying drawings, in which.

DETAILED DESCRIPTION OF THE PREFERRED EMBODIMENTS

Figure 1:
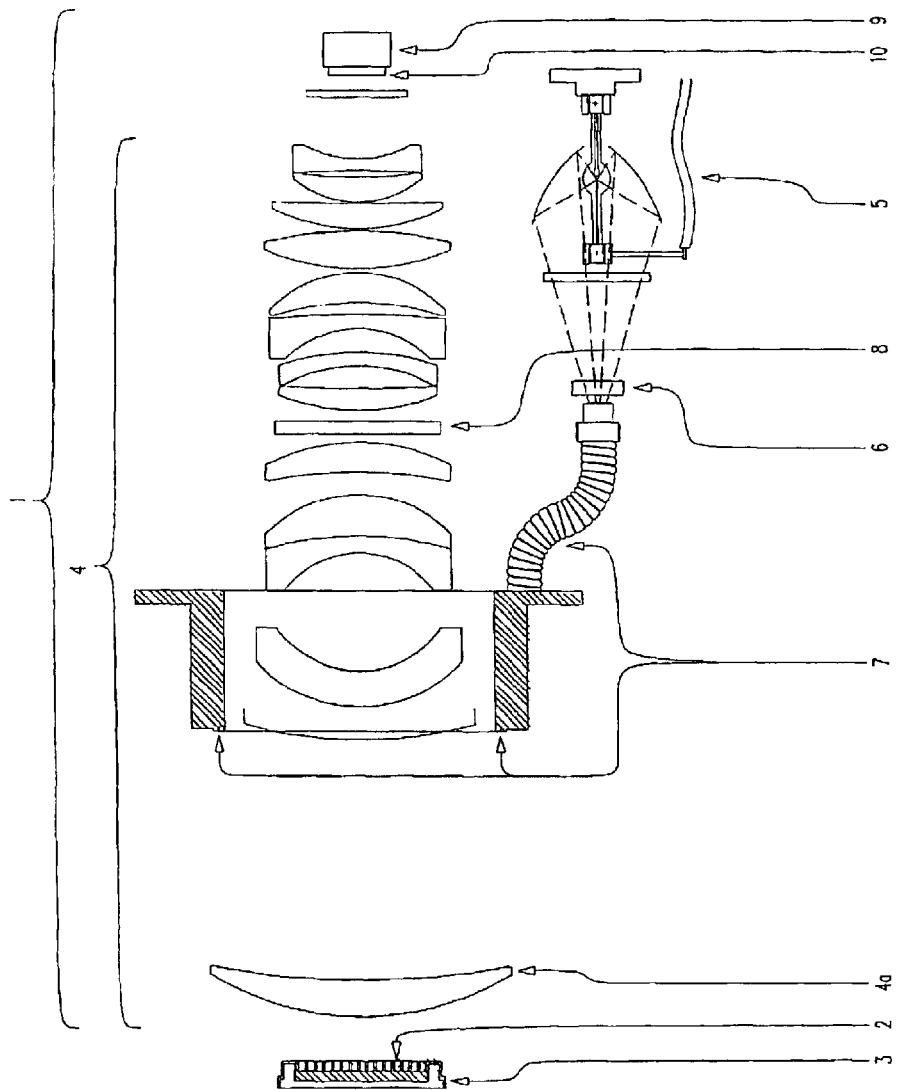
FIG. 1 is a cross-sectional schematic view of a preferred embodiment of an optical system in accordance with the present invention useful for fluorescence imaging.

FIG. 1 shows an optical system 1 in cross section, as used for fluorescence imaging of a plurality of wells 2 contained within a microwell plate 3. Major components of optical system 1 are a lens system 4, a pulsed light source 5, a primary excitation filter 6, a ring illuminator 7, a primary emission filter 8 (to remove wavelengths that are irrelevant to the desired sample signal), and a CCD camera system 9. Lens system 4 of optical system 1 comprises front element 4a operating in telecentric space, and forming an image of well plate 3 onto CCD detector 10 of CCD camera 9.

In operation, light source 5 provides the necessary light energy to be applied to the specimens within the wells 2. Preferably, the light source can be modulated from a high intensity to less than 1% of the high intensity in a time of less than 100 microseconds. The light from the source is transmitted through filter 6 and conducted via a light guide, such as a fiber optic bundle or a liquid light guide, to ring illuminator 7, internal to the lens system, which ring illuminator performs epi-illumination, preferably illuminating an area greater than 25 cm. sq. Light energy emitted by a specimen excited by epi-illumination is transmitted through lens 4a and the entire lens system 4 to camera 9, where an image is formed on the CCD detector 10.

Figure 2:
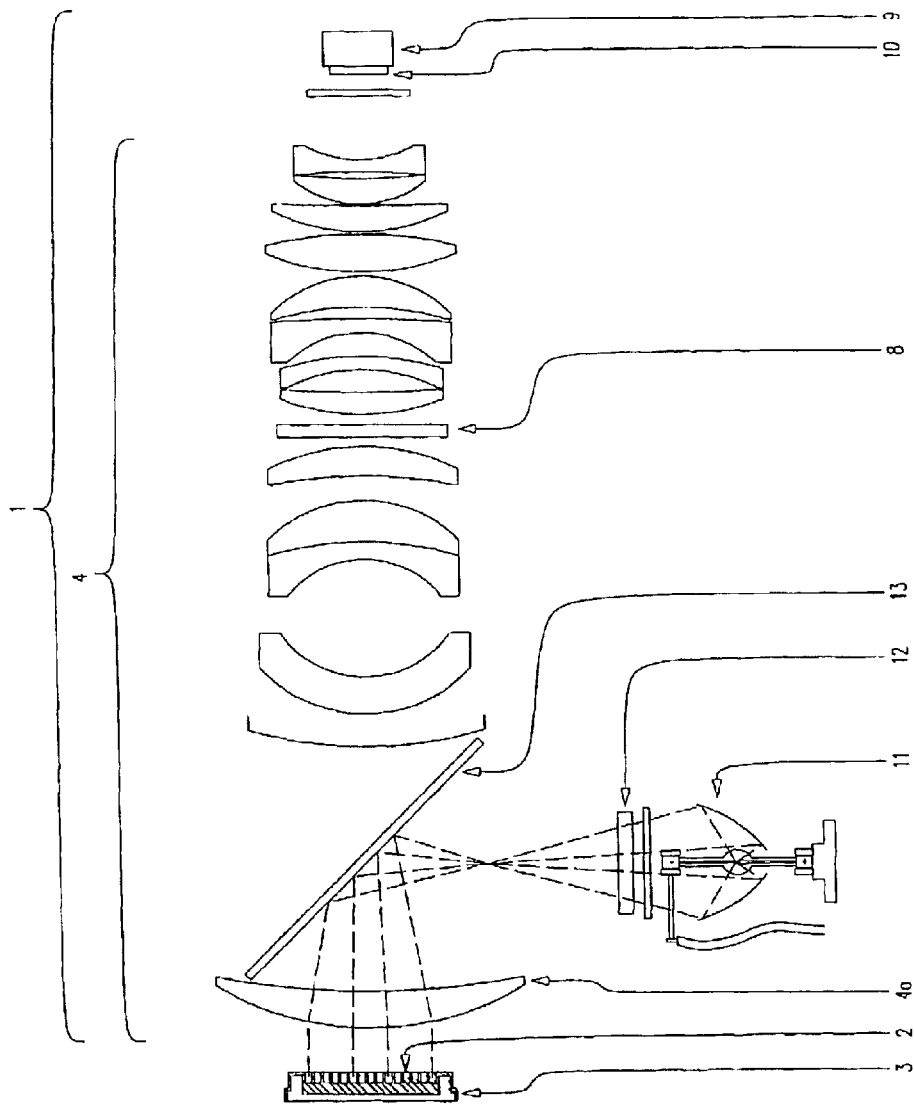
FIG. 2 is a cross-sectional view of an optical system as in FIG. 1 with the ring illuminator replaced by an epitaxial illumination system.

FIG. 2 repeats FIG. 1, with the replacement of the ring illuminator by an epitaxial illumination system. The epitaxial illumination is composed of a pulsed light source 11, a primary excitation filter 12 and a dichroic mirror 13 to reflect the excitation wavelengths onto the sample and transmit the wavelengths emitted from a specimen towards the camera.

Figure 3:
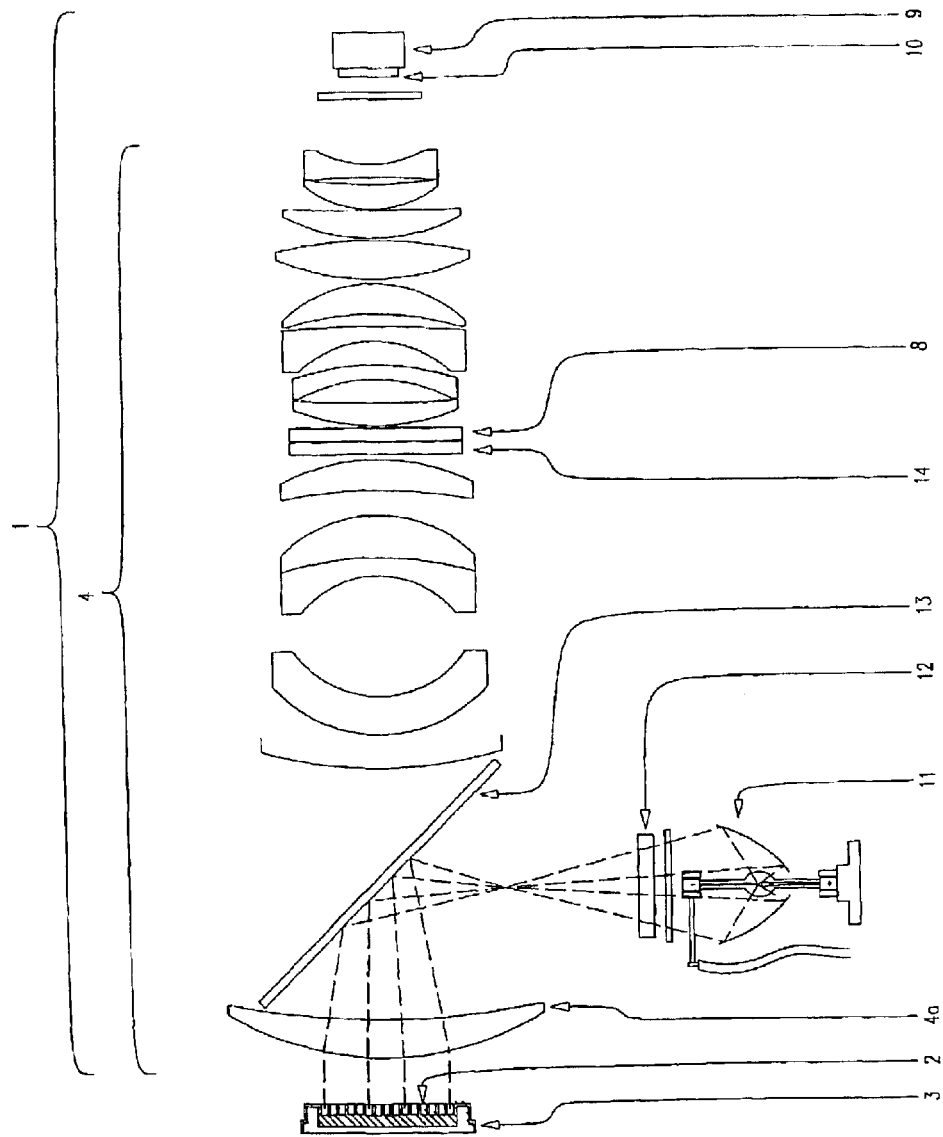
FIG. 3 is a cross-sectional view similar to FIG. 2 showing the addition of a fast shutter.

FIG. 3 repeats FIG. 2, with the addition of the fast shutter 14. Shutter 14 lies in close proximity to emission filter 8, at a position where all the rays are close to the optical axis. Preferably the shutter 14 is made of a material which can be made opaque (off) or transparent (on), with an on-off period shorter than 100 microseconds and with a contrast ratio in excess of 200:1. It is also preferred that the shutter be more than 20% transmissive at wavelengths of light between 500 and 700 nanometers. In a preferred embodiment, Shutter 14 is a FLC device, but the principle of applying a fast acting electronic shutter within the emission path is general, and Shutter 14 could be any other fast acting electronic shutter. For example, Shutter 14 could be implemented with an input polarizer composed of a piezoelectric material that changes the rotation of polarization depending on the electric field, and a polarizing analyzer, placed between sample 3 and CCD camera 9.

Figure 4:
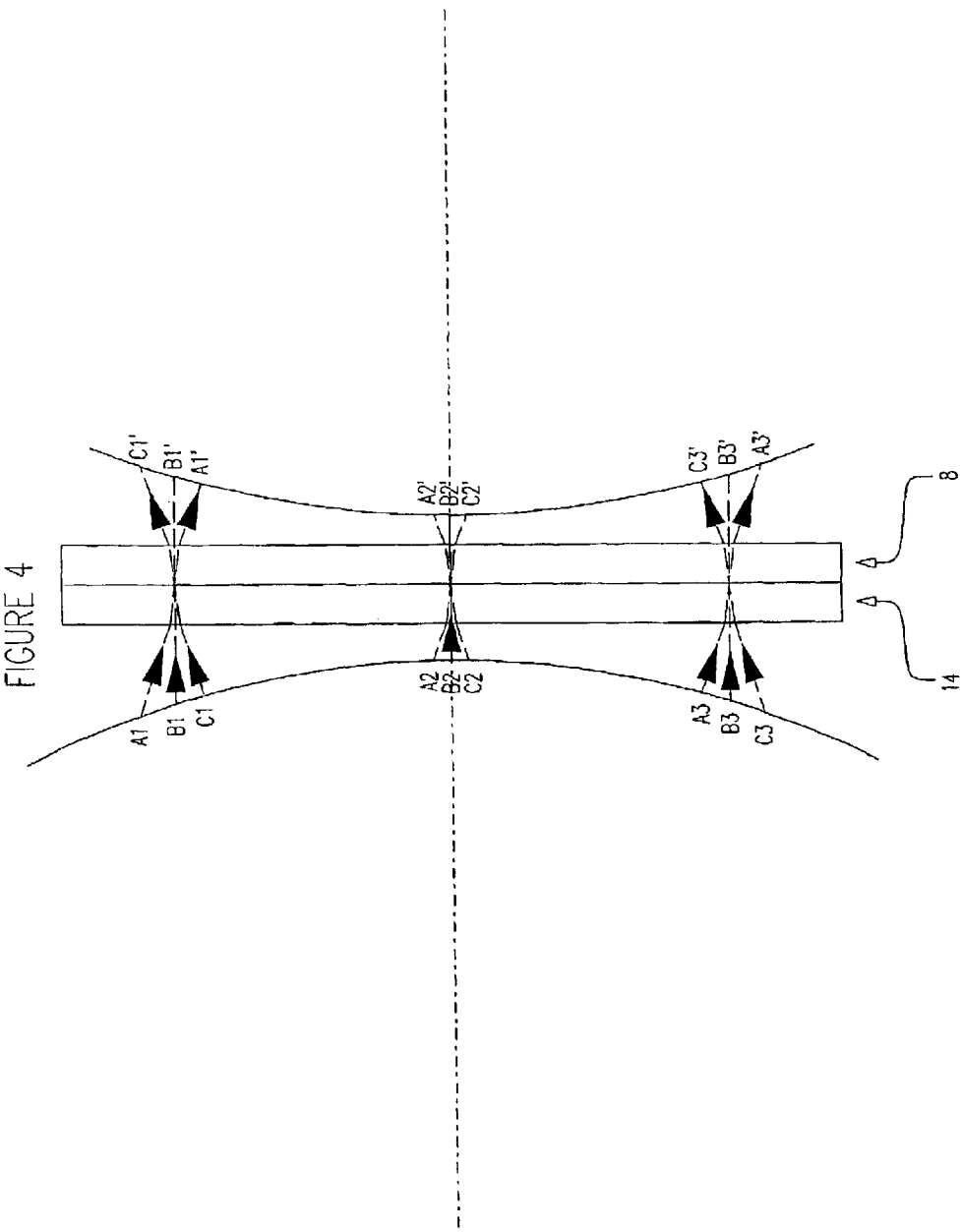
FIG. 4 is a light ray diagram illustrating the operation of the shutter and filter in the optical system.

FIG. 4 shows how rays A1–A3, which originate from one point at one corner of the plate, then pass through fast shutter 14 and emission filter 8. Also shown are rays B1–B3 and rays C1–C3, which originate from the center and opposite corner of the plate, respectively. Shutter 14 and filter 8 are in a position calculated to be the infinite conjugate position with respect to plate 3 as imaged through lens 4. Shutter 14 and filter 8 are so located that: a) the angles at which emission rays (as shown by rays A1'–A3', B1'–B3', and C1'–C3') pass through the optical axis of filter 8 are both close to the normal to the surface of filter 8, and are centered around the normal to filter 8, and b) the distribution of rays from plate 3 onto filter 8 is uniform. In the configuration shown, the system of the present invention is able to minimize spectral shifts arising from the actions of emission filter 8, when the filter is of the interference kind. It is a property of this embodiment, that the emission filter is in the infinite conjugate position of the lens 4, that beams also strike shutter 14 at a small angle to the normal, has beneficial properties that: a) the contrast ratio of shutter 14 is maximal; b) the size of emission filter 8 and of shutter 14 are minimized for a given maximum incidence angle; and c) the effect of unavoidable shutter 14 point defects will be distributed uniformly throughout the detector, without producing bright or dark spots in the image created on detector 10.

Figure 5:
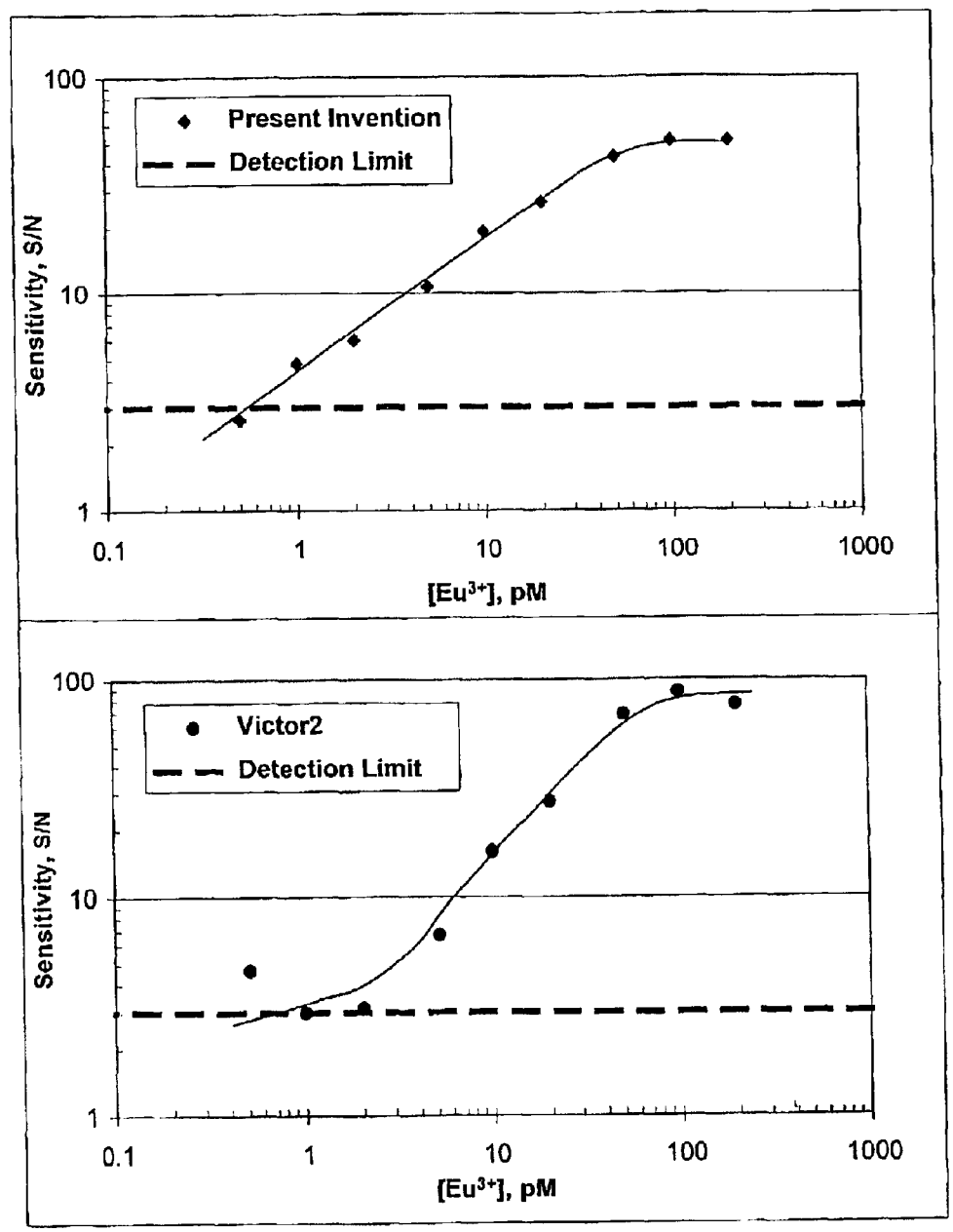
FIG. 5 illustrates graphs comparing the performance of a system in accordance with the present invention compared with a non-imaging, time resolved fluorometer.

FIG. 5 shows performance of the system of the present invention, as compared with a non-imaging time resolved fluorometer (in this case exemplified by a Wallac Victor 2 (Perkin Elmer Life Sciences) equipped with optimal components for time resolved fluorescence. The detection limit for Europium is defined by a signal to noise ratio of 3:1, and is similar for both instruments. If anything, the present invention provides superior performance near the detection limit.

Figure 6:
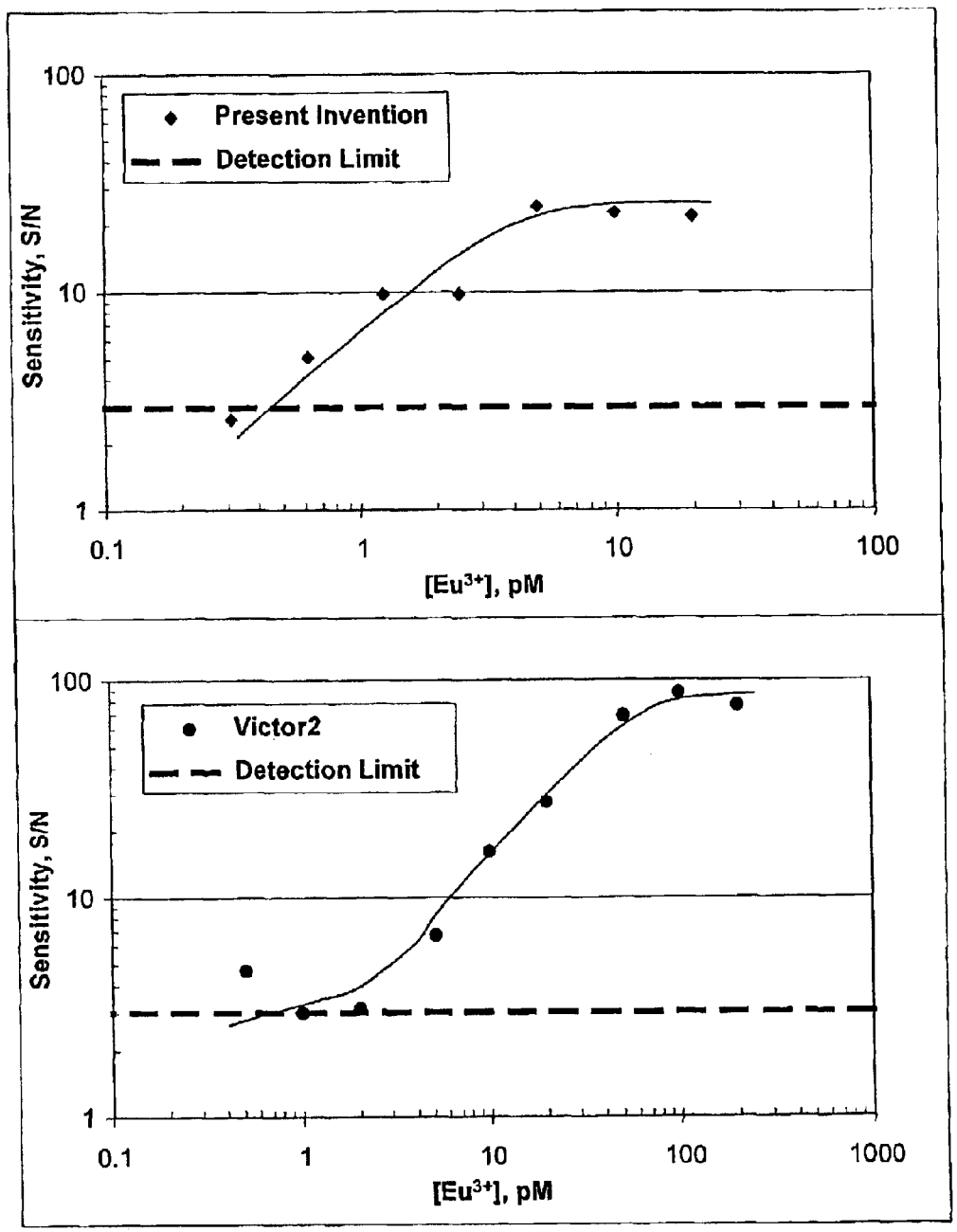
FIG. 6 illustrates graphs comparing the performance of an electron bombarded CCD camera implemented within the current system and a non-imaging, time resolved fluorometer.

FIG. 6 shows performance of an electron bombarded CCD camera (Hamamatsu), as implemented within the system of the present invention. In this case, gating is accomplished within the electron bombarded CCD detector as opposed to by the use of a fast electronic shutter mounted within lens 4. In this configuration, performance is again equal to that of a nonimaging fluorometer. FIG. 6 illustrates that the system of the present invention can be implemented with multiple forms of electronic gating, whether by a shutter within the emission pathway or a gating mechanism implemented within the detection device.

From FIGS. 5 and 6 it will be appreciated that the present invention makes it possible to achieve performance in a time resolved imaging fluorometer system which is at least as good as the best nonimaging fluorometers.

Although preferred embodiments of the invention have been disclosed for illustrative purposes, those skilled in the art will appreciate that many additions modifications and substitutions are possible without departing from the scope and spirit of the invention as defined by the accompanying claims.

REFERENCES

1. Beverloo, H. B., van Schadewijk, A., van Gelderen-Boele, S. and Tanke, H. J. Inorganic phosphors as new luminescent labels for immunocytochemistry and time-resolved microscopy, Cytometry. 11:784–92 (1990).
2. Beverloo, H. B., van Schadewijk, A., Bonnet, J., van der Geest, R., Runia, R., Verwoerd, N. P., Vrolijk, J., Ploem, J. S. and Tanke, H. J. Preparation and microscopic visualization of multicolor luminescent immunophosphors, Cytometry. 13:561–70 (1992).
3. Gadella, T. W. J. Jr. and Jovin, T. M. Oligomerization of epidermal growth factor receptors on A431 cells studies by time-resolved fluorescence imaging microscopy. A stereochemical model of tyrosine kinase receptor activation, The Journal of Cell Biology 129:1543–1558 (1995).
4. Galbraith, W., Wagner, M. C. E., Chao, J., Abaza, M., Ernst, L. A., Nederlof, M. A., Hartsock, R. J., Taylor, D. L. and Waggoner, A. S., Imaging cytometry by multiparameter fluorescence, Cytometry 12:579–596 (1991).
5. Haggart, R. Cooled slow-scan charge coupled device imaging fluorometer, Analytical Chimica Acta 290:48–57 (1994).
6. Neri D., Prospero T., Petrul H., Winter G., Browne M. and Vanderpant L. Multipurpose high sensitivity luminescence analyzer (LUANA): use in gel electrophoresis. Biotechniques 20:708–13 (1996)
7. Ramm, P. Imaging Systems in Assay Screening, Drug Discovery Today 4:401–410 (1999).
8. Rigler, R. Fluorescence correlations, single molecule detection and large number screening applications in biotechnology, Journal of Biotechnology 41:177–186 (1995).
9. Seveus, L., Vaisala, M., Sandberg, M., Kuusisto, A., Harju, R., Salo, J., Hemmila, I., Kojola, H. and Soini, E. Time-resolved fluorescence imaging of europium chelate label in immunohistochemistry and in situ hybridization, Cytometry 13:329–338 (1992).
10. Shotton, D. M. Electronic Light Microscopy—Present Capabilities and Future Prospects. Histochemistry and Cell Biology 104: 97–137 (1995).
11. Vereb, G., Jares-Erijman, E., Selvin, P. R. and Jovin, T. M. Temporally and Spectrally Resolved Imaging Microscopy of Lanthanide Chelates. Biophysical Journal 74 (5), 2210–2222 (May 1998)
12. Verwoerd N. P., Hennink E. J., Bonnet J., Van der Geest C. R. and Tanke, H. J. Use of ferro-electric liquid crystal shutters for time-resolved fluorescence microscopy. Cytometry Jun. 1, 1994;16(2):113–7.

We claim:

1. An imaging system for time resolved fluorometry of chemical, biological and medical samples provided on a containing medium where they are to be subjected to illumination, causing them to emit light, the imaging system comprising:
   an illumination source which can be modulated from substantially full intensity at the samples to less than approximately 1% of full intensity in a time of less than approximately 100 microseconds;
   an illumination system providing illumination from the source to an area in the vicinity of the samples which can be larger than a microscope field of view;
   a lens to collect light emitted from samples contained within the illuminated area;
   an image formation device located such that light from the samples, passing through the lens, impinges on the device and the device produces a representation of an image of the sample emissions;
   a shutter placed between the samples and the image formation device, comprising a structure which can be made opaque (off) or transparent (on), with an on-off period shorter than approximately 100 microseconds and with a contrast ratio between on and off in excess of approximately 100:1; and
   a control device for setting the on-off times of the illumination source and the open/close times of the shutter.

2. The system of claim 1, wherein the shutter is a ferroelectric crystal device configured as a polarizer that changes the rotation of polarization of light passing through it depending on an applied electric field.

3. The system of claim 2, further comprising a polarizing analyzer inserted in the emission path between the samples and the imaging formation device.

4. The system of claim 3, wherein the shutter is disposed within the lens, in a position to yield the best possible contrast ratio.

5. The system of claim 4, wherein the lens has optics so constructed and the shutter is so positioned in the optical path of the emitted light that the incidence angles of the light with respect to the normal onto the shutter do not exceed 20°.

6. The system of claim 3, wherein the containing medium is composed of a plurality of wells arranged within a plate and the lens is constructed to detect the entire contents of wells without parallax error.

7. The illumination system of claim 3, wherein the illumination source is a flash lamp.

8. The system of claim 3, wherein the control device is constructed to operate the shutter and the illumination source through multiple on-off cycles, the image formation device accumulating the light impinging thereon during plural cycles.

9. The imaging system of claim 3, wherein emitted light exhibits a decay in intensity and the shutter is gated on and off more than once during the decay following an illumination of the samples, so as to acquire images at different times during the decay process.

10. The system of claim 3 wherein the illumination system is constructed to guide light from the source into the lens and out of the lens towards the samples.

11. The system of claim 3 wherein the illumination system comprises a beam splitter between the lens and the samples constructed to reflect light from the source towards the samples and to transmit light emitted from the samples towards the lens.

12. The system of claim 3 further comprising a correction processor storing a leakage image of prompt fluorescence with the shutter closed and subtracting this stored leakage image from a subsequent delayed fluorescence image, to produce a corrected delayed fluorescence image.

13. The system of claim 2, wherein the shutter is disposed within the lens, in a position to yield the best possible contrast ratio.

14. The system of claim 13, wherein the lens has optics so constructed and the shutter is so positioned in the optical path of the emitted light that the incidence angles of the light with respect to the normal onto the shutter do not exceed 20°.

15. The system of claim 1, wherein the shutter is disposed within the lens, in a position to yield the best possible contrast ratio.

16. The system of claim 15, wherein the lens has optics so constructed and the shutter is so positioned in the optical path of the emitted light that the incidence angles of the light with respect to the normal onto the shutter do not exceed 20°.

17. The system of claim 2, wherein the containing medium is composed of a plurality of wells arranged within a plate and the lens is constructed to detect the entire contents of wells without parallax error.

18. The illumination system of claim 2, wherein the illumination source is a flash lamp.

19. The system of claim 2, wherein the control device is constructed to operate the shutter and the illumination source through multiple on-off cycles, the image formation device accumulating the light impinging thereon during plural cycles.

20. The imaging system of claim 2, wherein emitted light exhibits a decay in intensity and the shutter is gated on and off more than once during the decay following an illumination of the samples, so as to acquire images at different times during the decay process.

21. The system of claim 2 wherein the illumination system is constructed to guide light from the source into the lens and out of the lens towards the samples.

22. The system of claim 2 wherein the illumination system comprises a beam splitter between the lens and the samples constructed to reflect light from the source towards the samples and to transmit light emitted from the samples towards the lens.

23. The system of claim 2 further comprising a correction processor storing a leakage image of prompt fluorescence with the shutter closed and subtracting this stored leakage image from a subsequent delayed fluorescence image, to produce a corrected delayed fluorescence image.

24. The system of claim 1, wherein the containing medium is composed of a plurality of wells arranged within a plate and the lens is constructed to detect the entire contents of wells without parallax error.

25. The illumination system of claim 1, wherein the illumination source is a flash lamp.

26. The system of claim 1, wherein the control device is constructed to operate the shutter and the illumination source through multiple on-off cycles, the image formation device accumulating the light impinging thereon during plural cycles.

27. The imaging system of claim 1, wherein emitted light exhibits a decay in intensity and the shutter is gated on and off more than once during the decay following an illumination of the samples, so as to acquire images at different times during the decay process.

28. The system of claim 1 wherein the illumination system is constructed to guide light from the source into the lens and out of the lens towards the samples.

29. The system of claim 1 wherein the illumination system comprises a beam splitter between the lens and the samples constructed to reflect light from the source towards the samples and to transmit light emitted from the samples towards the lens.

30. The system of claim 1 further comprising a correction processor storing a leakage image of prompt fluorescence with the shutter closed and subtracting this stored leakage image from a subsequent delayed fluorescence image, to produce a corrected delayed fluorescence image.

* * * * *